United States Patent [19]

Dick et al.

[11] 4,070,354
[45] Jan. 24, 1978

[54] POLYMERS FROM N-(2-HYDROXYETHYL)AZIRIDINES

[75] Inventors: Clarence R. Dick; James Larry Potter, both of Lake Jackson, Tex.

[73] Assignee: The Dow Chemical Company, Midland, Mich.

[21] Appl. No.: 292,928

[22] Filed: Sept. 28, 1972

Related U.S. Application Data

[63] Continuation-in-part of Ser. No. 57,798, July 23, 1970, abandoned.

[51] Int. Cl.² .................... C07D 203/12; C08G 73/04
[52] U.S. Cl. .............................. 260/239 E; 260/2 EN
[58] Field of Search .................... 260/239 E, 2 EN

[56] References Cited

U.S. PATENT DOCUMENTS

| | | | |
|---|---|---|---|
| 2,475,068 | 7/1949 | Wilson | 260/2 EN |
| 2,626,931 | 1/1953 | Bestian | 260/2 EN |
| 3,531,527 | 9/1970 | Li et al. | 260/239 E |
| 3,583,977 | 6/1971 | Velzmann | 260/2 EN |
| 3,752,854 | 8/1973 | Tomalia et al. | 260/2 EN |

Primary Examiner—Henry R. Jiles
Assistant Examiner—Robert T. Bond
Attorney, Agent, or Firm—G. R. Plotecher; L. Wayne White

[57] ABSTRACT

Aziridinyl-terminated polymers containing the recurring unit

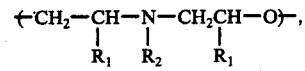

wherein $R_1$ is hydrogen or methyl and $R_2$ is hydrogen or a side chain of like structure, are prepared by warming N-(2-hydroxyethyl)- or N-(2-hydroxypropyl)ethyleneimine or -propyleneimine. Generally, the reaction is conducted in the presence of an alkali metal and at least trace amounts of water. The polymers are useful as curing agents for epoxy resins.

1 Claim, No Drawings

POLYMERS FROM N-(2-HYDROXYETHYL)AZIRIDINES

CROSS-REFERENCE TO RELATED APPLICATION

The present application is a continuation-in-part of our previous application Ser. No. 57,798, filed July 23, 1970, now abandoned.

BACKGROUND OF THE INVENTION

The monomers of this invention are known compounds prepared by reacting aziridine (ethylenimine) or 2-methylaziridine (propylenimine) with ethylene oxide or propylene oxide.

Previous attempts to polymerize the N-(2-hydroxyethyl)aziridines have resulted in polymerization occurring through the aziridine ring, exclusive of the hydroxyl group. E.g., the polymerization of N-(2-hydroxyethyl)aziridine, in water, catalyzed by a Bronsted acid (e.g. HCl) resulted in the production of a polymer having the repeating unit {CH$_2$CH$_2$-N (CH$_2$CH$_2$OH)}. The polymer was free of any residual aziridinyl groups.

SUMMARY OF THE INVENTION

It has now been discovered that novel aziridinylterminated polymers containing the recurring unit

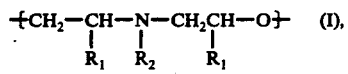

wherein R$_1$ is hydrogen or methyl and R$_2$ is hydrogen or a branching side chain of like structure, are prepared in the novel process comprising polymerizing by heating N-(2-hydroxyethyl)ethylenimine, N-(2-hydroxypropyl)ethylenimine, N-(2-hydroxyethyl)propylenimine and/or N-(2-hydroxypropyl) propylenimine. The majority of the terminal groups are aziridinyl groups, i.e.

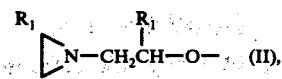

wherein R$_1$ has the aforesaid meaning, and hydroxyl groups. The polymers are useful as curing agents for epoxy resins.

The subject polymers all bear at least one terminal aziridinyl group and have a molecular weight of from 173 to about 3000. Their structure is represented by the formula

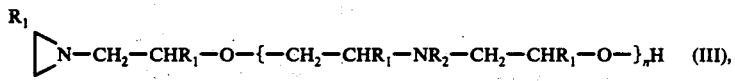

wherein R$_1$ and R$_2$ have the above meaning and $n$ is an integer of from 1 to about 25. When the polymerization process is conducted under essentially anhydrous conditions and for short or moderate reaction times, polymers are produced which are represented by (III) wherein R$_2$ is hydrogen and $n$ is an integer from 1 to about 4. The higher polymers are branched polymers which are obtained by longer reaction times and/or by including a trace amount of water in the process to catalyze the polymerization; the degree of branching increases with increasing molecular weight and with increasing reaction times. Such branching is a result of the fact that the polymer backbone contains a plurality of secondary amino nitrogen atoms bearing active amino hydrogen; such amino groups can compete with the hydroxyl groups for the aziridine reactant.

While the preferred method of preparing the subject polymers is to use the monomer(s) in as nearly anhydrous state as is possible, small amounts of water may be present (up to 5-10 percent by weight, based on the aziridine reactant (s)).

As the amount of water increases, the mechanism by which polymerization occurs evidently changes. With increasing amounts of water, polymers are obtained which contain, in addition to (I), the recurring unit —CH$_2$—CHR$_1$—N(CH$_2$—CHR$_1$—OH)— in increasing amounts.

Suitable reaction temperatures are from about 100° C. to about 225° C. with temperatures from about 160° C. to about 190° C. being preferred. However, at temperatures less than 160° C. the reaction rate is quite low. The pressure and the atmosphere above the reaction are not critical and atmospheric or superatmospheric pressures are suitable.

The process may be conducted in an inert solvent, such as xylene, diethylbenzene, etc., if desired. When the reaction is conducted in an inert medium, the conversion is lowered and the polymer produced has a lower molecular weight.

The rate of conversion is increased by including a small amount (up to about 1 percent by weight, based on the aziridine reactant(s)) of an alkali metal, such as lithium, sodium and potassium, or a derivative thereof, in the process. Examples of suitable such alkali metals and their derivatives include: metallic lithium, sodium or potassium; lithium amide, sodium amide or potassium amide; lithium, sodium or potassium borohydride; lithium, sodium or potassium amalgam; lithium, sodium or potassium hydride; alkali metal alkoxides, such as lithium or sodium methoxide, sodium ethoxide, and the like; sodium phenolate; alkyl derivatives of lithium, such as methyllithium, ethyllithium, butyllithium, and the like; and other like compounds and mixtures thereof.

Apparently, this effect on the rate of conversion is the sole effect, since the molecular weight of the polymer produced in a given reaction time is substantially the same regardless of the amount of alkali metal catalyst used.

The reaction time is determined largely by the particular polymer desired. The conversion increases with increasing reaction time. Low molecular weight polymers which are substantially linear are obtained at reaction times of from about 3-12 hours. Reaction times longer than 12 hours, e.g. 24-48 hours, result in higher conversions and yield a branched polymer.

SPECIFIC EMBODIMENTS

The following examples further illustrate the invention:

EXAMPLES 1-6

N-(2-Hydroxyethyl)aziridine (556 g., 6.4 moles), dried by distillation over sodium, was charged to a reaction vessel equipped with a means for stirring and a distillation head. The aziridine reactant contained less than 200 p.p.m. water. The system was purged with dry, carbon dioxide-free nitrogen. The mixture was warmed to 170° - 190° C. and maintained at that temperature for 24 hours. The unreacted monomer was then removed by distillation under reduced pressure. The conversion of monomer to polymer was 72%. The average molecular weight ($\overline{M}n$) of the polymer was determined by quantitative infrared (IR) analysis for the aziridine and hydroxyl end groups by using N-(2-hydroxyethyl)aziridine as the standard. The polymer was further characterized by analysis for tertiary nitrogen and molecular weight via the ebulliometric technique in isopropanol. The results were: 9.7% aziridinyl and 7.9% hydroxyl groups; 3.91% tertiary nitrogen (percents by weight based on the total composition); and an average molecular weight of 433 by IR and 420 by ebulliometry. The molecular weight based on hydroxyl content was found to be 215. A polymer of the following structure is supported:

$$\text{[N}-CH_2CH_2-O-CH_2CH_2-NH-CH_2CH_2-O-CH_2CH_2-\underset{|}{N}-CH_2CH_2-O-CH_2CH_2-\underset{|}{NH}$$
$$HO-CH_2CH_2-NH-CH_2CH_2 \quad\quad HO-CH_2CH_2$$

In like manner, five other runs were conducted as follows:

TABLE I

| No. | Time (Hrs.) | Temp. (° C.) | Monomer Converted (%) | IR Analysis %Az | IR Analysis %OH | $\overline{M}n^*$ (Az) | $\overline{M}n^*$ (OH) |
|---|---|---|---|---|---|---|---|
| 2 | 3.25 | 162 | 9.3 | 22.6 | 10.8 | 186 | 185 |
| 3 | 7.00 | 170 | 18.7 | 17.5 | ** | 240 | ** |
| 4 | 12.50 | 190 | 40.7 | 17.4 | 7.4 | 241 | 230 |
| 5 | 29.00 | 167–92 | 71.9 | 9.7 | 7.9 | 433 | 215 |
| 6 | 48.00 | 190 | 78.6 | 9.2 | 7.8 | 457 | 218 |

*$\overline{M}n^*$ = Average molecular weight was determined via IR analysis for both the aziridine (Az) end group and the hydroxyl content (OH), using N-(2-hydroxyethyl)-aziridine as the standard.
**Not measured.

Runs carried out by polymerizing the monomer in approximately 50% solution in diethylbenzene or xylene for periods of time in excess of 48 hours gave conversions of 10–11%; the molecular weights of these polymers, despite the lengthy reaction time, were in the range of 225–270 by IR analysis of aziridine end groups.

In the IR molecular weight determination, the area under the curve of a characteristic aziridine peak is measured in the monomer and in the polymer. The molecular weight of the polymer is then determined by the equation:

Mole wt. (polymer) = {area (monomer)/area (polymer)} × Mole wt. (monomer).

In Table I, the molecular weight data, based on OH analysis, shows that some of the polymer chains are branched and that this branching increases with increasing molecular weight.

A product made in the manner of Run 5 and having a mol. wt. of 500 (111 g.) was mixed with 200 g. of epoxy resin (the reaction product of Bisphenol-A and epichlorohydrin; epoxide equivalent weight 186–192), cured at ambient temperature for 16 hours and finished by heating at 100° C. for 2 hours. The following data were obtained on the cured product:

a. The deformation temperature 51.5° C. ASTM D 648-56.
b. Average tensile strength, 4440 lb./in. and elongation, 5.5%. ASTM D-368-58T.
c. Flexural strength 5990 p.s.i. ASTM 790-59T.

EXAMPLES 7–13

The following runs were conducted as above except that the reaction time and temperature in each (except run 7) was 24 hours at 120° C., and the reactions were conducted in the presence of varying amounts of water in a sealed vessel. Run 7 was heated at the boiling point of the solution for 24 hours. The monomer used in this series of experiments was prepared under substantially anhydrous conditions using dry reactants and contained from 0.1 to 0.2 weight percent water.

TABLE II

| No. | Aziridine Reactant (g.) | Added Water (g.) | Monomer Converted (%) | IR Analysis % Aziridine | $\overline{M}n$ (A)* | $\overline{M}n$ (B)** |
|---|---|---|---|---|---|---|
| 7 | 50.00 | 50.00 | 100 | 0 | — | 2000 |
| 8 | 54.86 | 8.24 | 100 | 2.0 | 2100 | 1400 |
| 9 | 49.72 | 2.58 | 93.8 | 3.8 | 1152 | 1100 |
| 10 | 50.31 | 1.03 | 70.4 | 4.2 | 1000 | 890 |
| 11 | 49.33 | 0.48 | 43.8 | 5.2 | 807 | 860 |
| 12 | 49.43 | 0.25 | 46.6 | 5.6 | 750 | 860 |
| 13 | 52.40 | 0 | 27.8 | 5.5 | 763 | 795 |

*$\overline{M}n$ (A) average molecular weight via IR analysis for the aziridine end group.
**$\overline{M}n$ (B) average molecular weight via ebulliometry in isopropanol.

In Run 7, the polymer was analyzed by infrared analysis. It contained no detectable aziridinyl end groups and no ether linkages. Hence, the polymerization occurred exclusively through the aziridine ring.

EXAMPLE 14–16

The following runs were conducted in the presence of various amounts of sodium metal as a catalyst. The N-(2-hydroxyethyl)aziridine contained approximately 0.1% by weight water and was polymerized by heating the monomer in the presence of sodium metal for 24 hours at 190° C.

TABLE III

| Ex. | Sodium Conc.* | Mole Ratio (Monomer/Na) | Monomer Converted (%) | $\overline{M}n^{**}$ |
|---|---|---|---|---|
| 14 | 0.09 | 280/1 | 42 | 260 |
| 15 | 0.14 | 192/1 | 48 | 265 |
| 16 | 0.3 | 92/1 | 54 | 260 |

*Weight percent based on aziridine monomer.
**Average molecular weight via ebulliometry in isopropanol.

Analysis of the hydroxyl and aziridine groups in Examples 14–16, Table III gave substantially the same molecular weights as shown above. This indicates a substantially linear polymer was formed.

Similar results are obtained by replacing N-(2-hydroxyethyl)aziridine with N-(2-hydroxyethyl)-propylenimine. Copolymers are obtained by using a mixture of aziridine reactants. The polymers are useful as epoxy agents, as illustrated above.

We claim:
1. A process for preparing a polymer of the formula

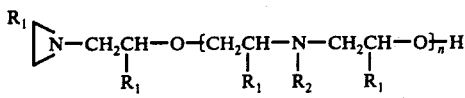

wherein $R_1$ is hydrogen or methyl, $R_2$ is hydrogen or a branching side chain of like structure, and $n$ is an integer of from 1 to 25, the process comprising polymerizing by heating at a temperature of from about 100° C to about 225° C at least one monomer selected from the group of N-(2-hydroxyethyl)ethylenimine, N-(2-hydroxypropyl)ethylenimine, N-(2-hydroxyethyl)-2-methylethylenimine or N-(2-hydroxypropyl)-2-methylethylenimine, said process being conducted in the presence of from zero percent up to about 10 percent by weight of water, based on the weight of the monomer(s), and in the presence of metallic lithium, sodium, potassium; or lithium, sodium or potassium amide; sodium or potassium borohydride; lithium, sodium, or potassium amalgam; lithium, sodium or potassium hydride; lithium sodium or potassium lower alkoxide having from 1 to 4 carbon atoms in the alkoxy radical; sodium phenolate; or an alkyllithium having from 1 to 4 carbon atoms in the alkyl radical.

* * * * *